US007448288B2

(12) United States Patent
Montefusco

(10) Patent No.: US 7,448,288 B2
(45) Date of Patent: Nov. 11, 2008

(54) SCENT EVIDENCE TRANSFER DEVICE

(76) Inventor: Vincent Montefusco, P.O. Box 387, Mammoth Lakes, CA (US) 93546

( * ) Notice: Subject to any disclaimer, the term of this patent is extended or adjusted under 35 U.S.C. 154(b) by 160 days.

(21) Appl. No.: 11/545,941

(22) Filed: Oct. 12, 2006

(65) Prior Publication Data
US 2008/0087110 A1 Apr. 17, 2008

(51) Int. Cl.
*G01N 1/14* (2006.01)
(52) U.S. Cl. .................................... 73/864.34
(58) Field of Classification Search .......... 73/864, 73/34; D10/80, 103
See application file for complete search history.

(56) References Cited
U.S. PATENT DOCUMENTS
D319,796 S * 9/1991 McGown et al. ............. D10/81
D397,051 S * 8/1998 Tolhurst et al. .............. D10/80

* cited by examiner

*Primary Examiner*—Hezron E. Williams
*Assistant Examiner*—Tamiko D Bellamy
(74) *Attorney, Agent, or Firm*—Irving Keschner

(57) ABSTRACT

An improved scent transfer device for collecting evidence at a crime scene. The device comprises an air inflator with a gas cartridge coupled to an air amplifier. A holder having a sterile pad positioned therein is secured to the air amplifier. When gas from the cartridge is expelled into the air amplifier, a vacuum is created at the end of the air amplifier where the pad holder is attached, enabling a user, when the pad holder is positioned near an area to be examined, to collect the scent on the pad. The pad can then be removed and stored in an evidence bag.

5 Claims, 3 Drawing Sheets

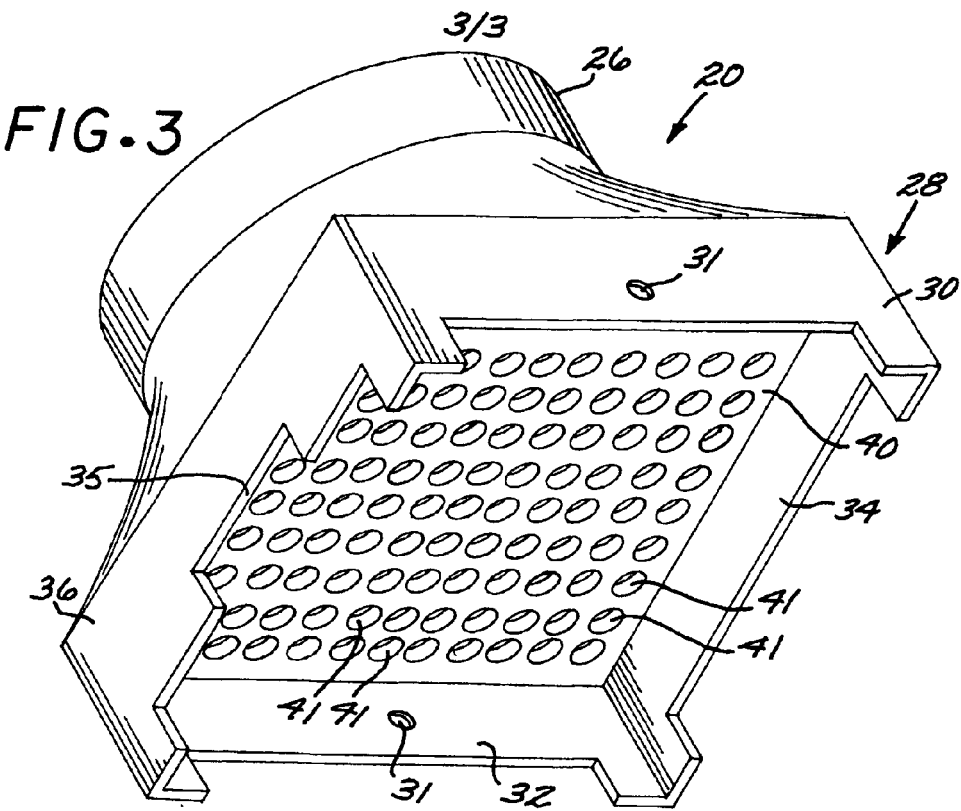
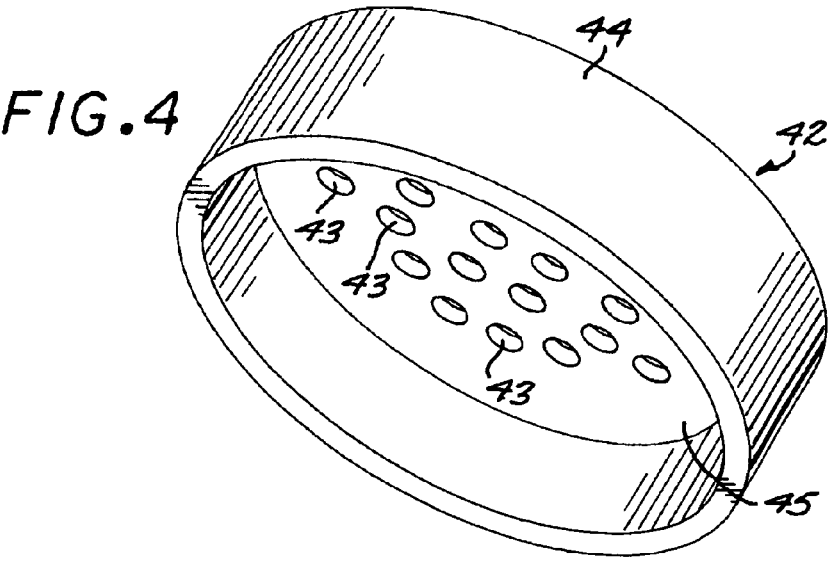

SCENT EVIDENCE TRANSFER DEVICE

BACKGROUND OF THE INVENTION

1. Field of the Invention

The present invention relates to a device for collecting scents from a scene and enabling trained dogs to sniff the collected scent and then hunt for criminals or missing persons.

2. Description of the Prior Art

U.S. Design Pat. No. 397,051, issued on Aug. 18, 1998, discloses a scent evidence device which includes a pad holder, the function of the device being to collect scent from a crime scene on a pad and thereafter make the pad available to a trained dog to hunt for criminals or missing persons.

Although the patented device works satisfactorily, it is relatively large and requires an electric motor to generate a vacuum.

What is desired is to provide a scent transfer device which is more compact than the prior art design and wherein an electric motor is not required to generate the required vacuum.

SUMMARY OF THE INVENTION

The present invention provides an improved scent transfer device for collecting evidence at a crime scene. The device comprises an air inflator having a gas cartridge, the inflator being coupled to an air amplifier. A holder having a sterile pad positioned therein is secured to the air amplifier. When gas from the cartridge is expelled into the air amplifier, a vacuum is created at the end of the air amplifier where the pad holder is attached, enabling a user to, when the pad holder is positioned near an area to be examined, to collect the scent on the pad. The pad can then be removed and stored in an evidence bag. The device of the present invention is light weight and does not require mechanical parts, such as a motor and batteries. In addition, the use of gas cartridges eliminates the necessity of using air to create the vacuum which could contaminate the pad and also enables the generated vacuum to be precisely metered each time the device is used.

DESCRIPTION OF THE DRAWINGS

For a better understanding of the present invention as well as other objects and further features thereof, reference is made to the following description which is to be read in conjunction with the accompanying drawing therein:

FIG. 3 shows the pad holder utilized in the scent transfer device of the present invention; and FIG. 4 illustrates an alternate embodiment of the pad holder utilized in the present invention.

DESCRIPTION OF THE INVENTION

Figure 1:
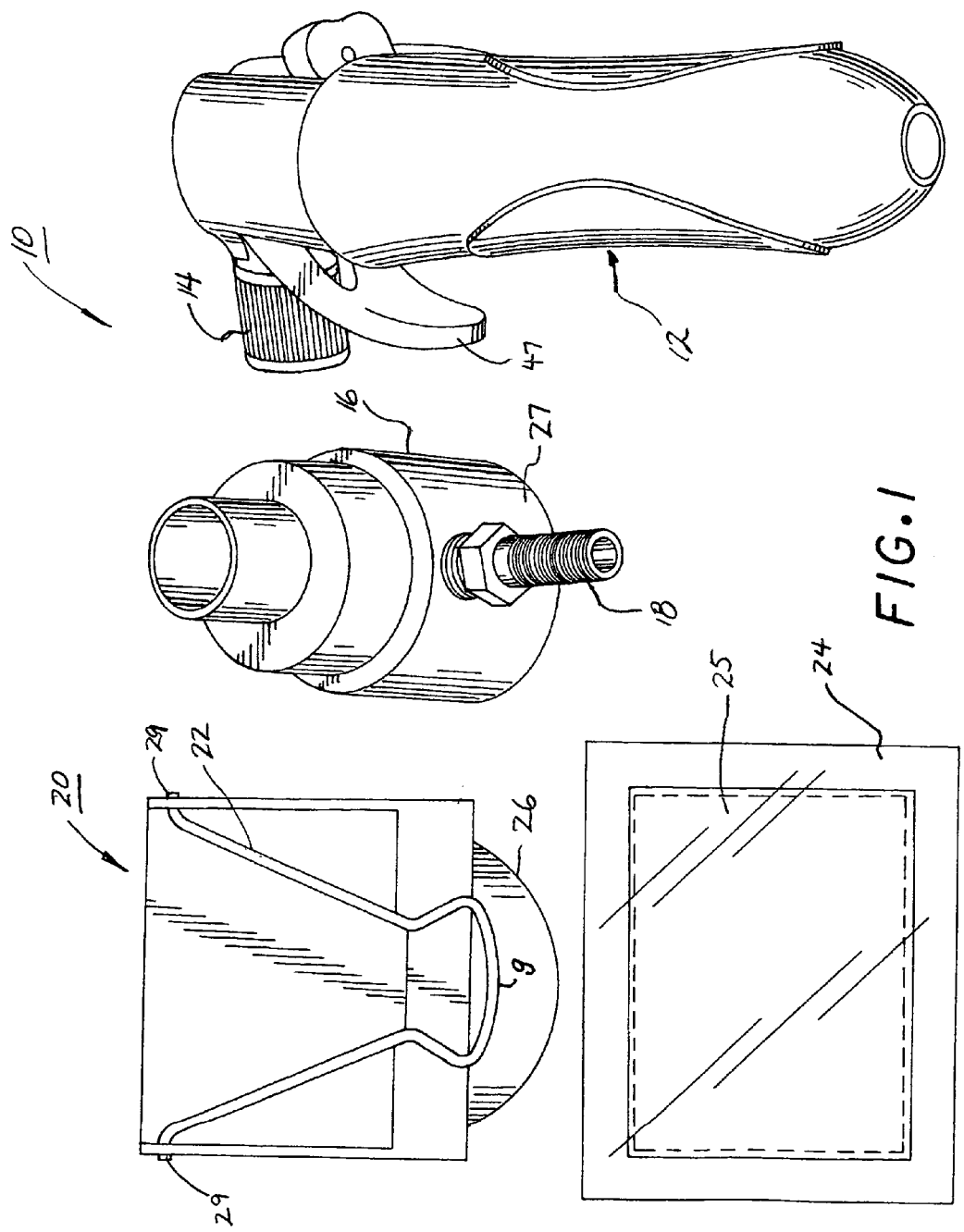
FIG. 1 illustrates the separate components which comprise the scent transfer device of the present invention.

Referring now to FIG. 1, the components forming the scent transfer unit 10 according to the teachings of the present invention is illustrated.

In particular, unit 10 comprises an air inflator 12, a brass fitting 14 attached to inflator 12, air amplifier 16 having a tube valve fitting 18 coupled thereto and pad holder device 20 having metal clip 22 coupled thereto. A package 24 containing a sterile pad 25 is illustrated, the sterile pad therein being removed and connected to device 20 by metal clip 22.

Figure 2:
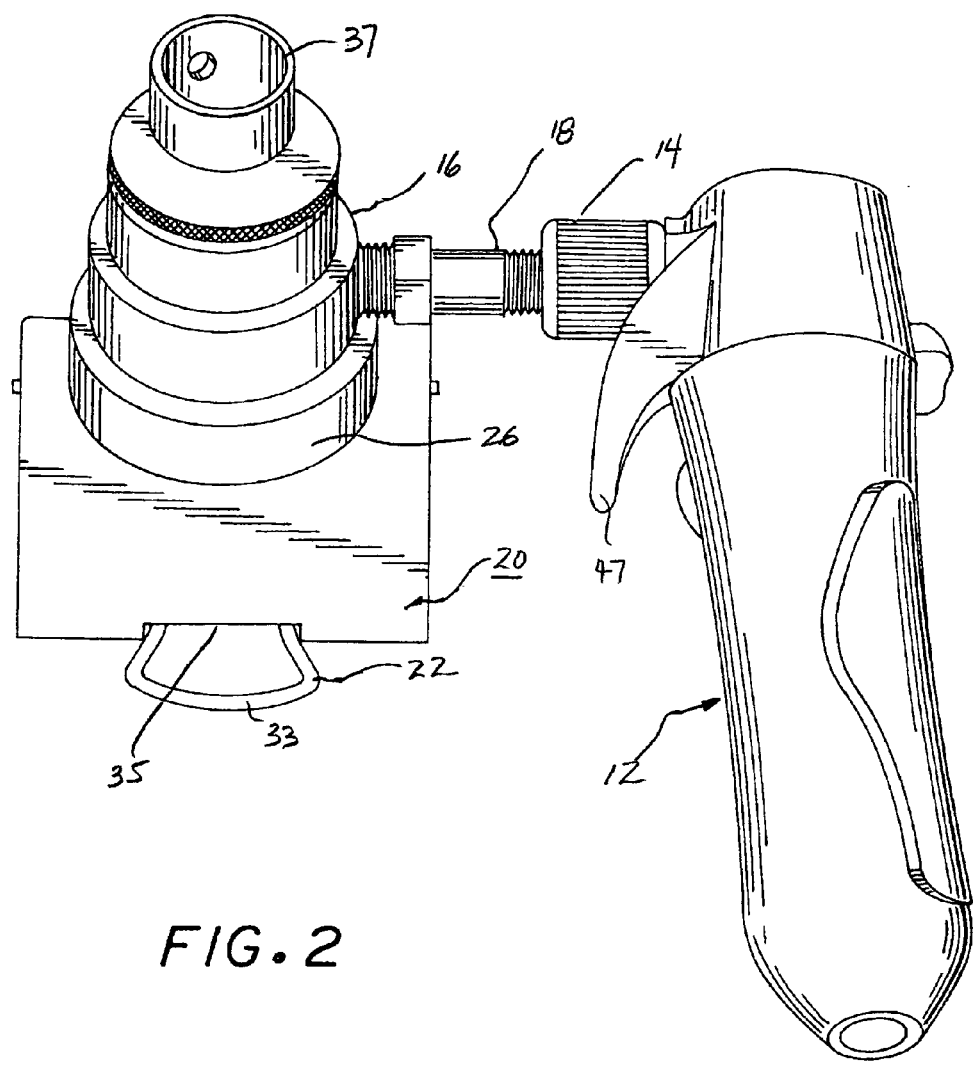
FIG. 2 illustrates the assembled components of FIG. 1.

FIG. 2 illustrates the components shown in FIG. 1 assembled together to form unit 10.

FIG. 3 illustrates in more detail pad holder device 20. Device 20 comprises a circular head portion 26 adapted to fit over the bottom, or skirt, portion 27 of air amplifier 16. The lower portion of device 20 comprises a square shaped housing portion 28 having sides 30, 32, 34 and 36 and base portion 40 having a plurality of apertures 41 formed therein. It should be noted that other pad holder shapes can be utilized, such as rectangular shapes. A sterile pad from package 24, when the unit 10 is ready for operation, is secured within housing portion 28 adjacent base portion 40 by metal clip 22 (the ends 29 of clip 22 extend into openings 31 formed in walls 30 and 32, clip head 33 resting in slot 35 formed in side 35 as illustrated).

FIG. 4 illustrates an alternate embodiment of the pad holder device 20. In particular, a cylindrically shaped lid, or cup, 42 having a plurality of openings 43 formed in base portion 44 is adapted to have a sterile pad positioned therein as member 42 is fitted over skirt portion 27 of amplifier 16.

Unit 10 operates as follows:

An inflator device 12, typically used to inflate bike tires, instead is designed to incorporate a gas cartridge therein to generate an air vacuum downstream. Preferably a cartridge having Argon gas is used since Argon prevents device 10 from freezing as the gas is expelled. It should be noted that other gases (as well as air) can be used, such as $CO_2$.

Brass fitting 14 at one end of the inflator 12 is screwed onto tire valve fitting 18 which in turn is mounted onto air amplifier 16 via fitting 17 as shown. Plastic sterile pad holder 20 is attached to the air amplifier 16 (pressed or screwed on) as shown.

The sterile pad 25 is loaded under the metal hold down clip 22 and snapped in place. Sterile pad 25 rests on the base 40 of holder 20, base 40 having a plurality of holes, or apertures, drilled into it to allow scent evidence to pass through. When the inflator valve 47 adjacent brass fitting 14 is pressed to initiate the scent collecting tests, gas is released into air amplifier 16 creating suction at the end where the head portion 26 is attached to holder 20. The other end 37 of the air amplifier 16 exhausts the gas. Suction is provided by the Venturi effect, created by the air flow through amplifier 16, an effect well known in the prior art. After the scent is collected, metal clip 22 is released and pad 25 removed from holder 20 and stored in a sterile collection bag.

An air amplifier 16 that has been successfully utilized is the Model 6040 sold by Exair Corporation, Cincinnati, Ohio; an inflator 12 which has been successfully utilized is the Ultra Flat Plus sold by Innovations in Cycling, Inc., Tuscon, Ariz.

Referring to FIG. 4, lid 42 is designed to be sold in a sterile paper pack for one-time use, the pack also including a sterile pad.

Lid 42 is made of a flexible material, such as rubber, and the sterile pad 25 (not shown) is removably secured on the inside surface 45 of lid 42. When the user has vacuumed up the scent evidence onto the sterile pad 25, lid 42 with pad 25 mounted thereto, is removed from air amplifier 16 and stored in an evidence bag together. Alternatively, the sterile pad 25 is removed from the lid 42 and then stored in a sterile collection bag without lid 42.

The inside diameter of the lid 42 is pressed fit onto the outside diameter of amplifier 16 for easy on and off operation.

It should be noted that devices 20 and 42 can be utilized with other type of vacuum systems, such as a battery powered vacuum device.

The inert gas cartridge utilized in inflator 12 described hereinabove is typically of a size to be used 1 to 3 times for the scent collection tests. If it is desired to conduct more tests before the cartridge needs to be replaced, a larger sized cartridge is required (i.e. a $CO_2$ or air cartridge used in the paintball gun industry will provide approximately 250 tests). In this case, inflator 12 is removed and a short line is used to connect amplifier 16 to a pressure regulator and the pressure regulator to the larger cartridge. The regulator controls the amount of vacuum amplifier 16 produces.

The present invention thus provides an improved lightweight scent transfer unit for use which precisely monitors the amount of vacuum generated each time the device is used, uses gas cartridges to provide the vacuum instead of ambient air, and requires no motors or batteries.

While the invention has been described with reference to its preferred embodiments, it will be understood by those skilled in the art that various changes may be made and equivalents may be substituted for elements thereof without departing from the true spirit and scope of the invention. In addition, many modifications may be made to adapt a particular situation or material to the teachings of the invention without departing from its essential teachings.

What is claimed is:

1. A device for collecting a scent comprising:
   a cartridge having pressurized gas contained therein;
   first means coupled to said gas cartridge, said first means having a member for controlling the expulsion of said pressurized gas and a attachment member;
   second means having first and second ends, said first end being coupled to said attachment member for receiving gas expelled from said gas cartridge; and
   a member for holding a pad member, said member being removably secured to the said second end of said second means, a vacuum being created at said second end of said second means when pressurized gas is introduced to said second means from said gas cartridge.

2. The device of claim 1 wherein said gas cartridge contains Argon gas.

3. The device of claim 1 wherein said pad is removably secured to said holding member by a clip.

4. The device of claim 1 wherein said holding member is removed from said second means and the holding member with the rod member secured thereto is stored in a collection device after the scent is collected.

5. The device of claim 1 wherein said pad member is removed from said holding member and stored in a collection device after the scent is collected.

* * * * *